United States Patent
Westerkamp

(10) Patent No.: US 11,389,613 B2
(45) Date of Patent: Jul. 19, 2022

(54) LINE SYSTEM FOR AN APPARATUS FOR THE RESPIRATING OF PATIENTS

(71) Applicant: ALCMAIR PARTNERS BV, Alkmaar (NL)

(72) Inventor: Bart Westerkamp, Alkmaar (NL)

(73) Assignee: LÖWENSTEIN MEDICAL TECHNOLOGY SA, Luxembourg (LU)

( * ) Notice: Subject to any disclaimer, the term of this patent is extended or adjusted under 35 U.S.C. 154(b) by 780 days.

(21) Appl. No.: 15/109,510

(22) PCT Filed: Jan. 5, 2015

(86) PCT No.: PCT/NL2015/000001
§ 371 (c)(1),
(2) Date: Jul. 1, 2016

(87) PCT Pub. No.: WO2015/105415
PCT Pub. Date: Jul. 16, 2015

(65) Prior Publication Data
US 2016/0325069 A1    Nov. 10, 2016

(30) Foreign Application Priority Data
Jan. 7, 2014   (NL) .................................... 1040590

(51) Int. Cl.
*A61M 16/08*    (2006.01)
*A61M 16/01*    (2006.01)
(Continued)

(52) U.S. Cl.
CPC ........ *A61M 16/0875* (2013.01); *A61M 16/00* (2013.01); *A61M 16/01* (2013.01);
(Continued)

(58) Field of Classification Search
CPC .. A61M 16/0875; A61M 16/00; A61M 16/01; A61M 16/0883; A61M 16/08;
(Continued)

(56) References Cited

U.S. PATENT DOCUMENTS 3,379,194 A * 4/1968 Ziermann ............ A61M 16/00
128/200.18
3,389,698 A    6/1968 Kadosch et al.
(Continued)

FOREIGN PATENT DOCUMENTS

GB         1107268 A    3/1968

OTHER PUBLICATIONS

International Search Report for corresponding International Application No. PCT/NL2015/000001.

*Primary Examiner* — Joseph D. Boecker
*Assistant Examiner* — Brian T Khong
(74) *Attorney, Agent, or Firm* — Egbert, McDaniel & Swartz, PLLC

(57) ABSTRACT

An apparatus for respirating a patient has a line system for a lead-through of respiratory or anaesthesia gas. The line system has a first connection for the patient, a second connection for input of the gas, and a third connection for discharge of gas. The line system is formed of plate-shaped first and second parts. The inner surface of the first and second parts face each other and are movable toward each other. A canal is formed on the inner surface and defines at least a portion of a flow-through pathway for the gas.

5 Claims, 12 Drawing Sheets

(51) Int. Cl.
*A61M 16/20* (2006.01)
*A61M 16/00* (2006.01)
*A61M 16/10* (2006.01)
*A61M 16/22* (2006.01)

(52) U.S. Cl.
CPC ........ *A61M 16/0883* (2014.02); *A61M 16/20* (2013.01); *A61M 16/22* (2013.01); *A61M 16/0057* (2013.01); *A61M 16/104* (2013.01); *A61M 2205/502* (2013.01); *A61M 2207/00* (2013.01); *A61M 2209/084* (2013.01)

(58) Field of Classification Search
CPC .. A61M 16/20; A61M 16/22; A61M 16/0057; A61M 16/021; A61M 16/0054; A61M 16/10; A61M 16/0891; A61M 16/0066; A61M 16/206; A61M 2205/12; A61M 2205/128; A61M 2209/084; A61M 2207/00; A61M 1/1621; F04B 43/113; F04B 43/02; F04B 43/12; Y10T 137/2234; B63C 11/18
See application file for complete search history.

(56) References Cited

U.S. PATENT DOCUMENTS

| | | | |
|---|---|---|---|
| 3,586,021 A | 6/1971 | McGuinness | |
| 3,687,137 A * | 8/1972 | Johnson | A61M 16/104 128/204.13 |
| 4,120,300 A * | 10/1978 | Tiep | A61M 16/10 128/204.24 |
| 4,603,691 A * | 8/1986 | Rusz | A61M 16/0057 128/205.15 |
| 5,378,126 A * | 1/1995 | Abrahamson | A61M 5/14224 417/413.1 |
| 5,549,105 A * | 8/1996 | Bloch | A61M 16/08 277/924 |
| 5,718,569 A * | 2/1998 | Holst | F04B 43/02 137/624.18 |
| 6,397,841 B1 * | 6/2002 | Kenyon | A61M 16/08 128/202.27 |
| 6,644,311 B1 * | 11/2003 | Truitt | A61M 16/0069 128/204.18 |
| 6,837,260 B1 * | 1/2005 | Kuehn | A61M 16/0057 128/204.18 |
| 2004/0069305 A1 * | 4/2004 | Niemela | A61M 16/20 128/205.24 |
| 2008/0202591 A1 * | 8/2008 | Grant | A61M 1/1037 137/12 |
| 2009/0090363 A1 * | 4/2009 | Niland | A61M 16/026 128/203.26 |
| 2011/0017212 A1 * | 1/2011 | Kenyon | A61M 16/0051 128/203.26 |
| 2011/0155132 A1 * | 6/2011 | Virr | A61M 16/0816 128/203.26 |
| 2011/0197884 A1 * | 8/2011 | Duff | A61M 16/024 128/204.21 |
| 2012/0232469 A1 * | 9/2012 | Medina | F04B 9/02 604/28 |
| 2012/0285454 A1 * | 11/2012 | Nibu | A61M 16/0066 128/204.18 |
| 2015/0059745 A1 * | 3/2015 | Barker | A61M 16/0066 128/203.14 |

\* cited by examiner

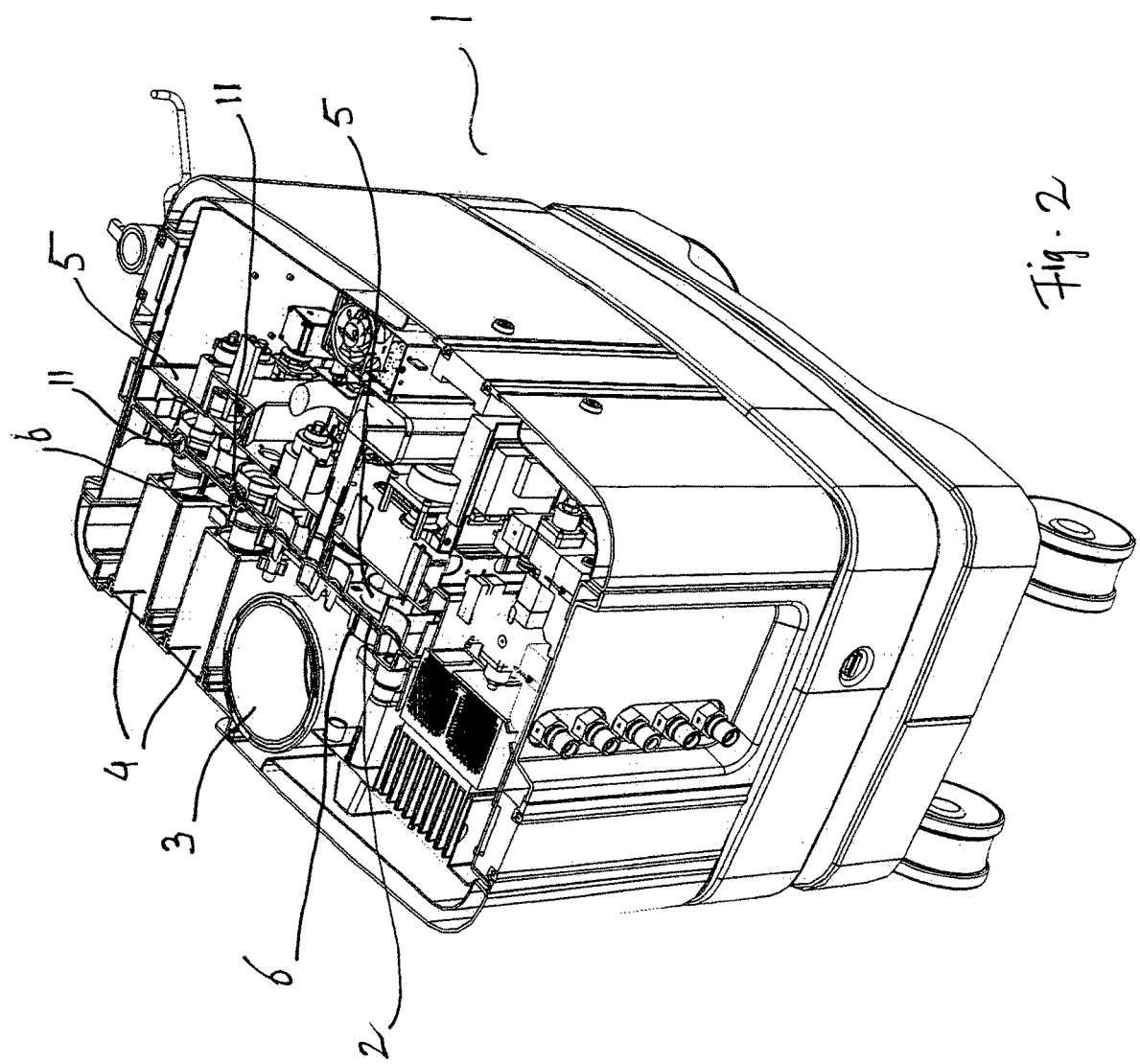

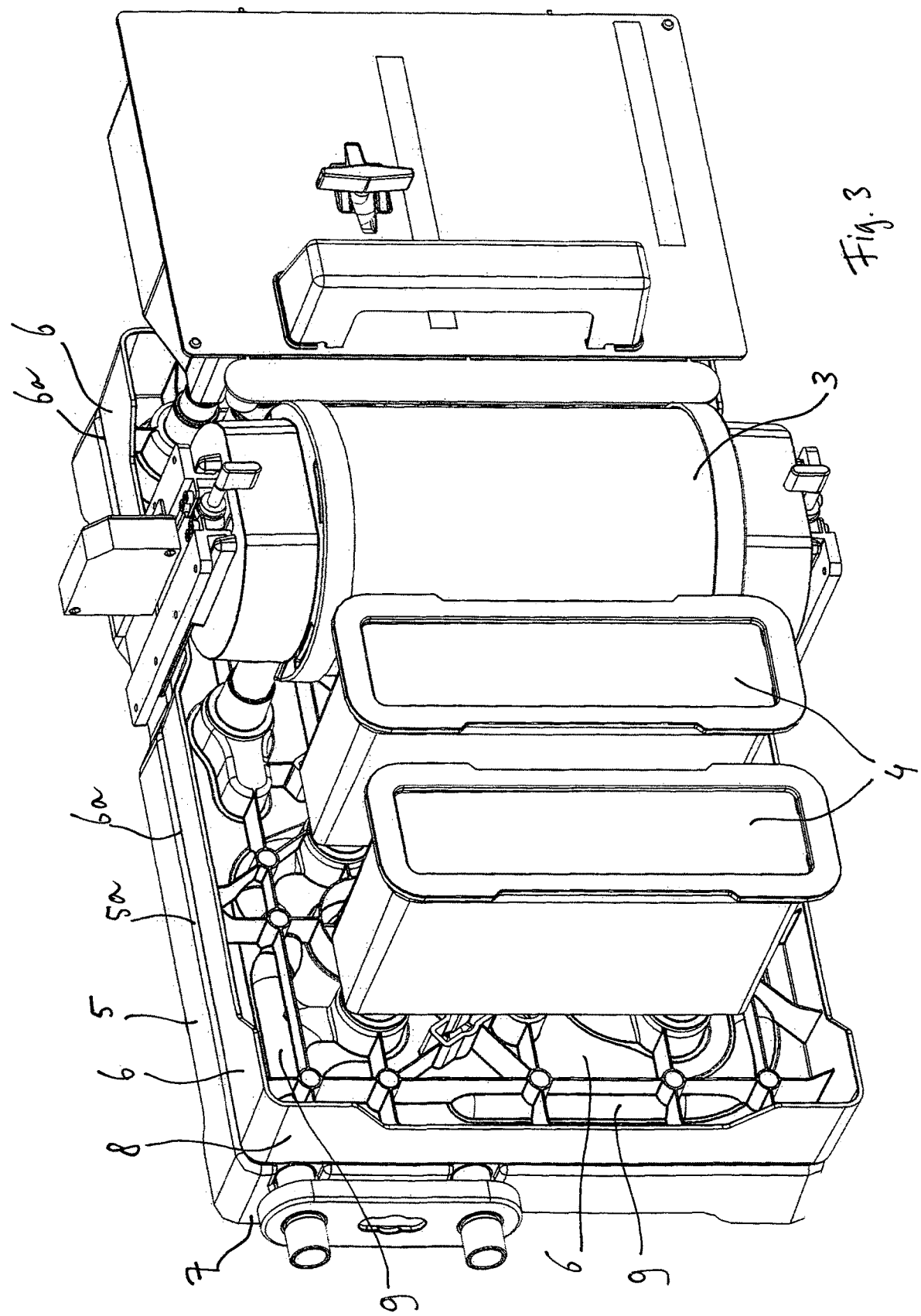

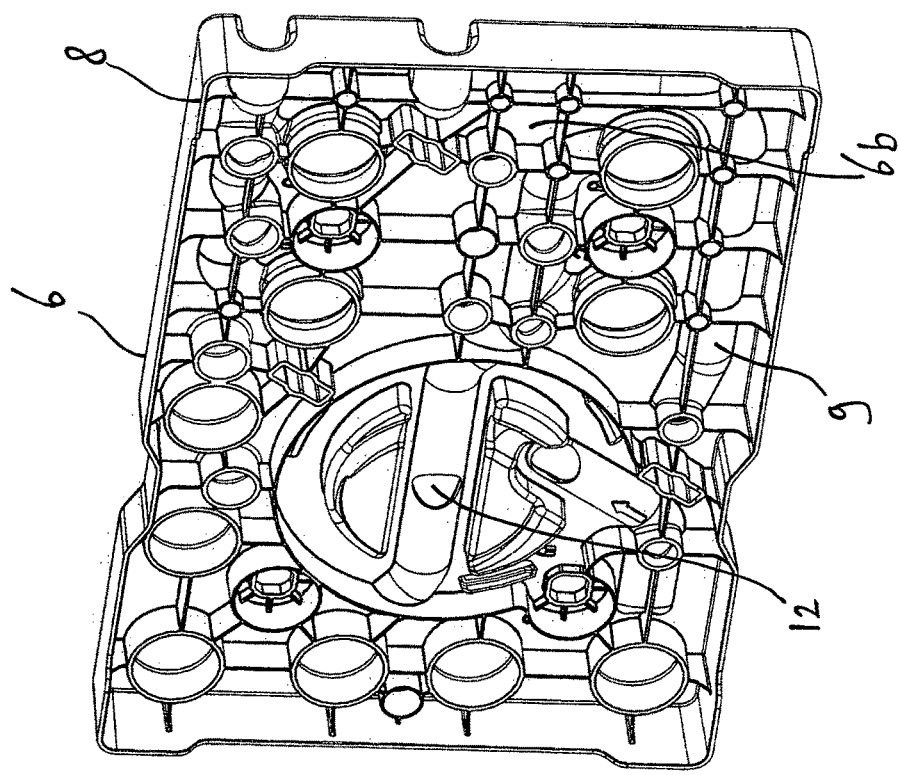
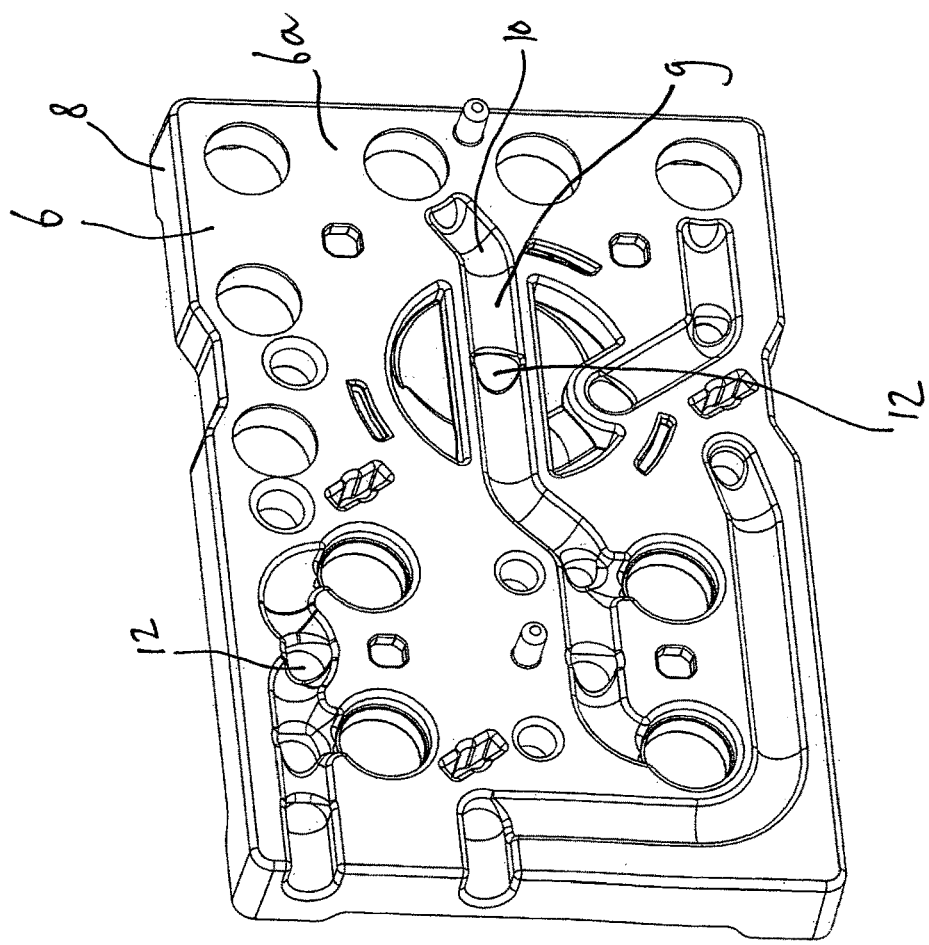

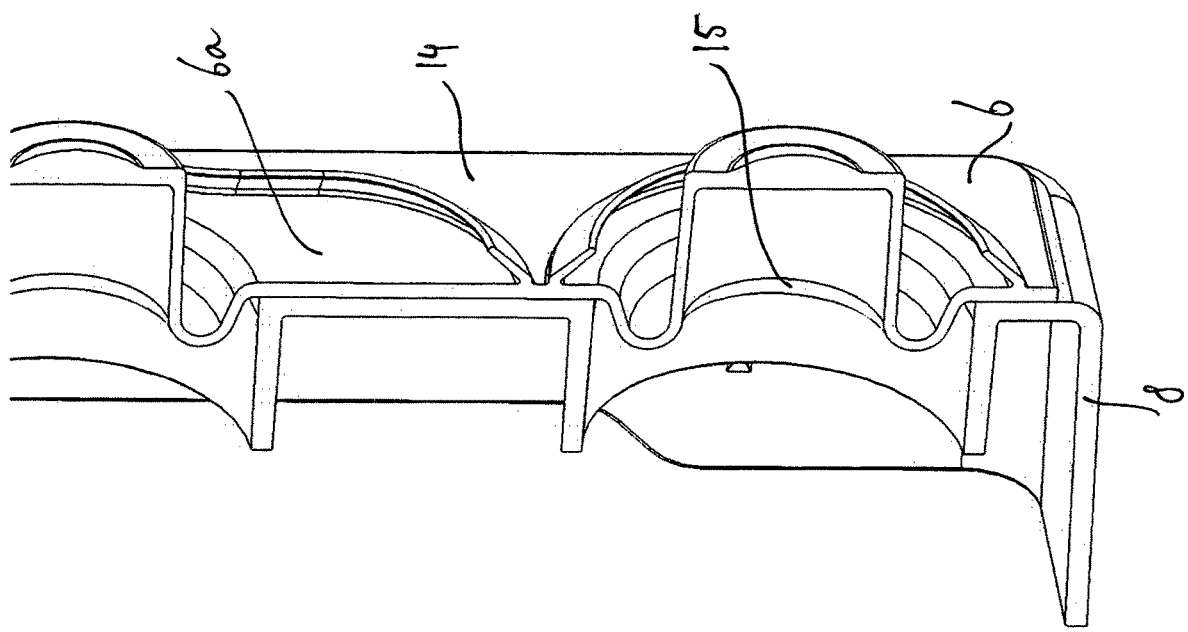

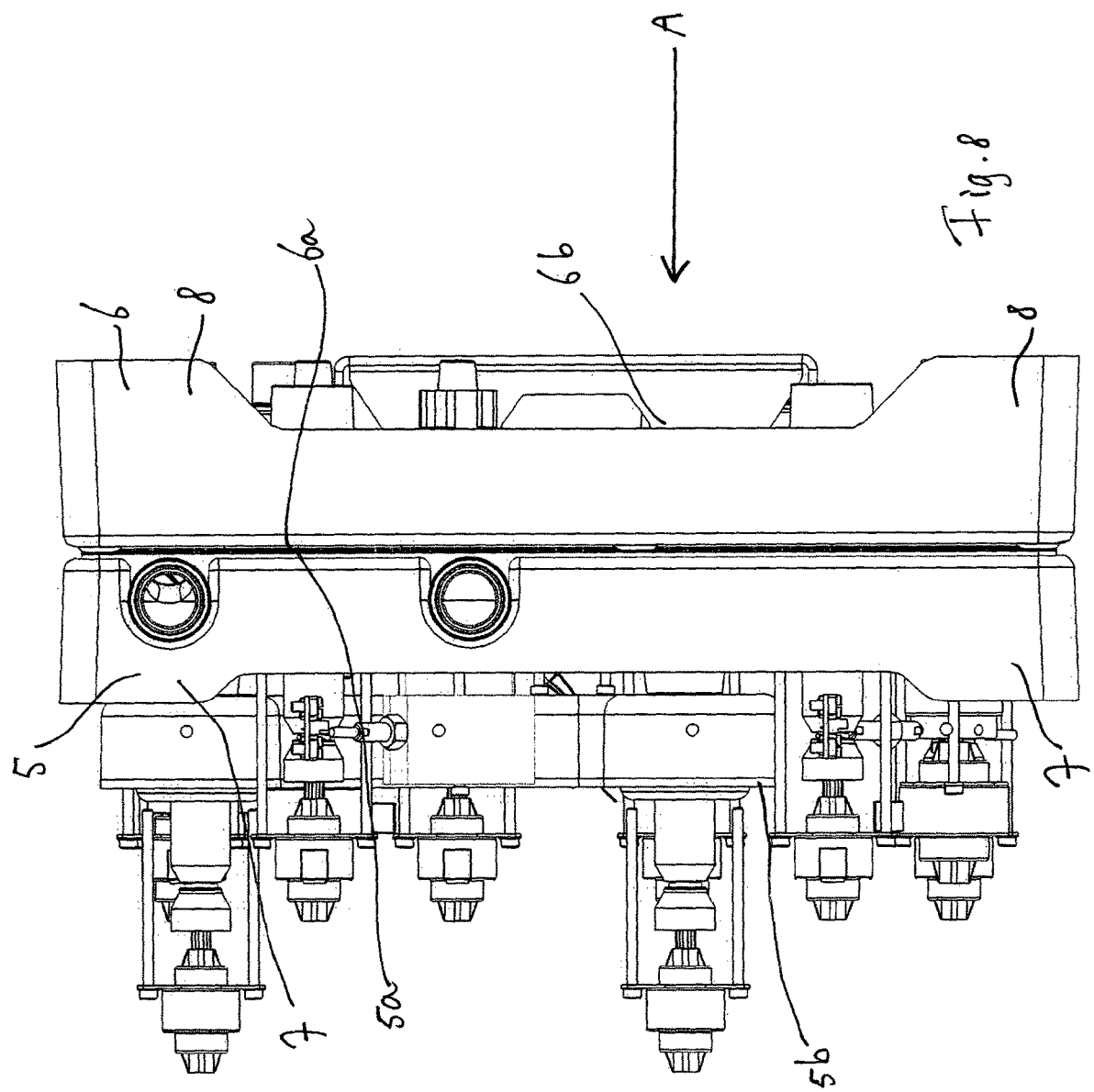

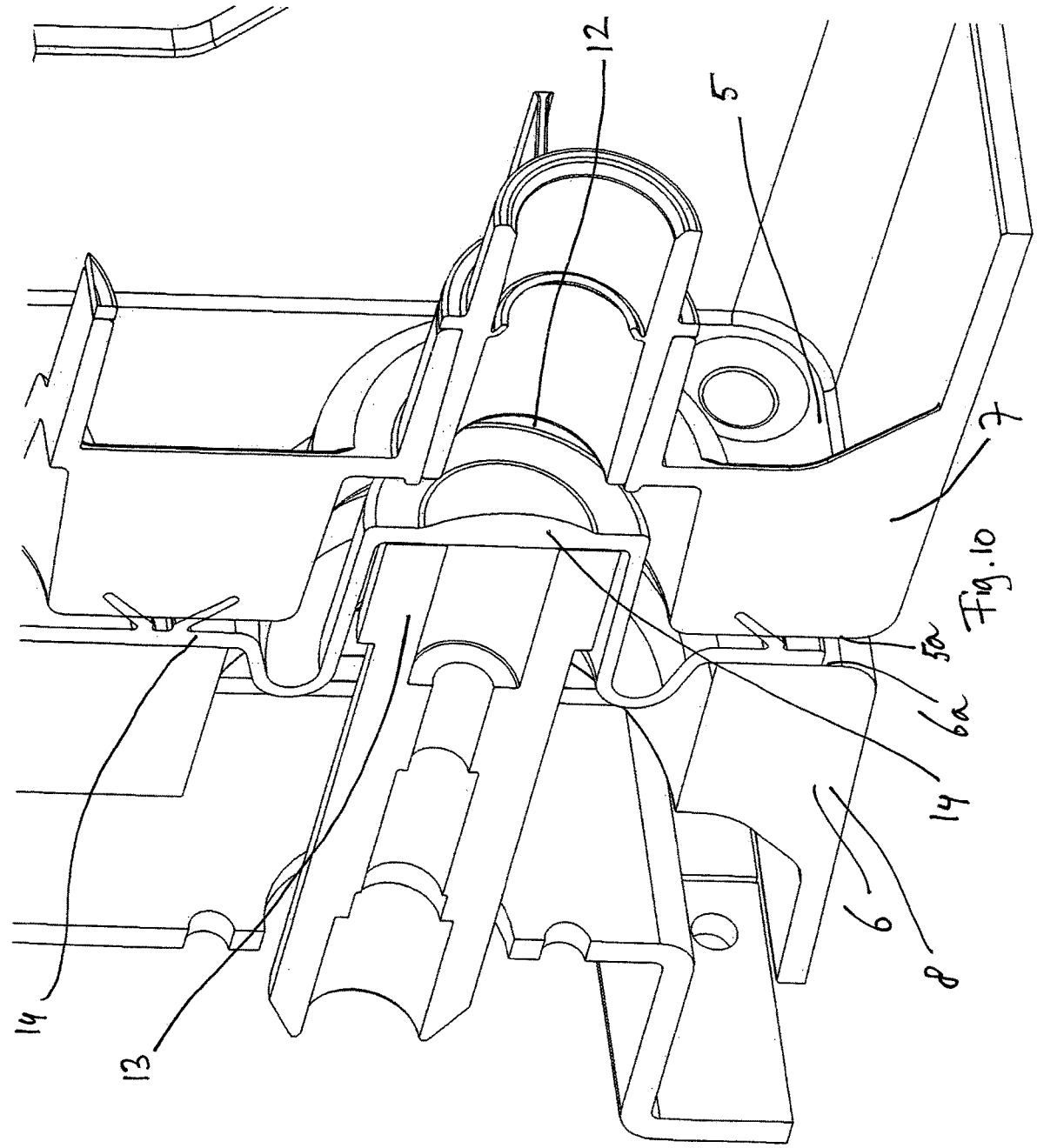

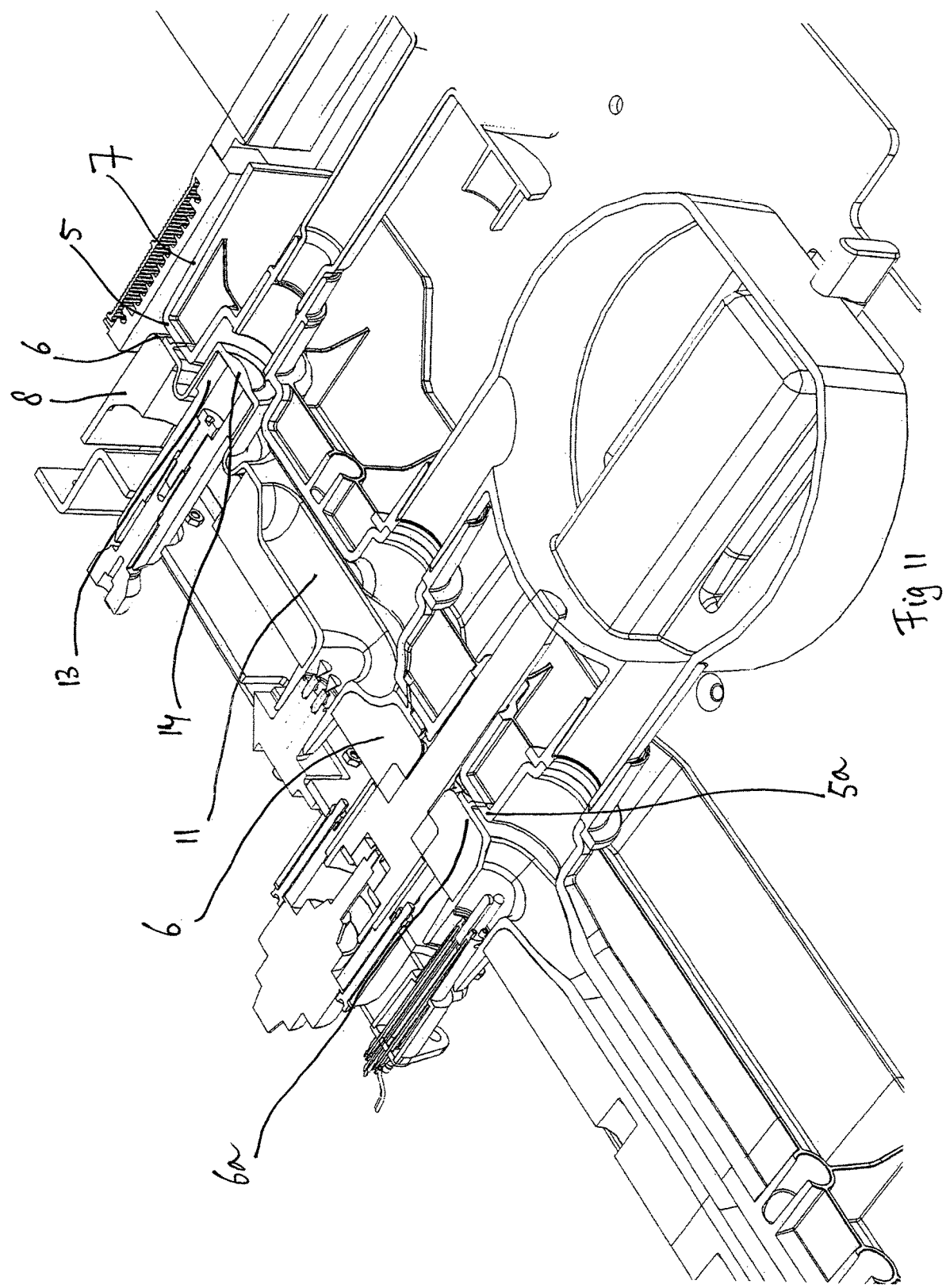

LINE SYSTEM FOR AN APPARATUS FOR THE RESPIRATING OF PATIENTS

CROSS-REFERENCE TO RELATED APPLICATIONS

The present application claims priority from International Application No. PCT/NL2015/00001, filed on Jan. 5, 2015 and claiming priority from Netherlands Application No. 1040590, filed on Jan. 7, 2014.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

INCORPORATION-BY-REFERENCE OF MATERIAL SUBMITTED ON COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to an apparatus for the respirating of patients, more particularly for ventilating at home, for anaesthesia or for intensive care, comprising a line system for the lead-through of respiratory gas, which line system is provided with a connection for the patient, with connections for the supply of the various components of the gas and with further connections for the discharge of the various components of the gas.

2. Description of Related Art Including Information Disclosed Under 37 CFR 1.97 And 37 CFR 1.98

In the known apparatus the line system is formed by hoses.

In order to avoid contamination of a next patient by the apparatus, the known hose system, particularly the inner side thereof, needs to be thoroughly cleaned. This is done by cleaning the hoses in water with a detergent, after which the inner side of the hose is flushed. After this, one lets the line system drain or one shakes this out. Then the system has to be dried completely.

Because the inner side of the hoses is difficult to attain or not attainable at all, the cleaning and drying thereof is rather difficult.

BRIEF SUMMARY OF THE INVENTION

The invention aims to provide an apparatus with a line system that can be cleaned and dried in a simple manner.

The apparatus, according to the invention, thereto is characterized in that the line system, in whole or in part, is built up of a first and a second, substantially plate-shaped, part, each having an inner surface and an outer surface, whereby the first part and the second part are intended to be placed with their inner surfaces against each other, whereby in the inner surface of at least one of the parts, a canal is formed, having a longitudinal side that is open towards the inner surface, such that, during placement thereon of the inner surface of the other part the open side of the canal is covered and a flow-through pathway is formed through which the respiratory or anaesthetic gas can be led.

According to the invention, a canal is provided in the inner surfaces of both parts, having a longitudinal side that is open towards the inner surfaces, such that, during placement of the inner surfaces of the parts against each other, the open sides of the canals abut one another and the canals form a flow-through pathway through which the respiratory or anaesthesia gas can be led.

According to the invention, the first and/or the second part are provided along at least a part with a side edge that has been flanged towards the outer surface.

According to the invention, the first and/or the second part are provided with openings.

According to the invention, a canal connects to or is in communication with an opening.

According to the invention, at the location of an opening, a closing means is provided, that is displaceable into the flow-through pathway for the opening and closing off of parts of the flow-through pathway.

According to the invention, the inner surface of at least one of the parts is provided with a layer of material, more in particular, a silicone material.

Further characteristics and particulars will be described with reference to the drawings of an example of an embodiment of the apparatus according to the invention.

BRIEF DESCRIPTION OF THE SEVERAL VIEWS OF THE DRAWINGS

FIG. 2 shows a perspective view of the apparatus according to FIG. 1, open at the top.

FIG. 3 shows a perspective view of a line system as incorporated in the apparatus according to FIG. 1, with connected thereto a few further parts of the respirating apparatus.

FIGS. 5a and 5b show a perspective view of an inner surface respectively outer surface of the second part 6 of the line system.

FIG. 7 shows in detail a perspective view of the inner surface of the second part with a silicone lining thereon.

FIG. 8 shows a side view of the parts such as these are placed against each other.

FIG. 10 shows a perspective view, in cross-section, of the parts such as these are placed against each other, with a closing means.

FIG. 11 shows a further perspective view, in cross-section, of the parts such as these are placed against each other.

DETAILED DESCRIPTION OF THE INVENTION

Figure 1:
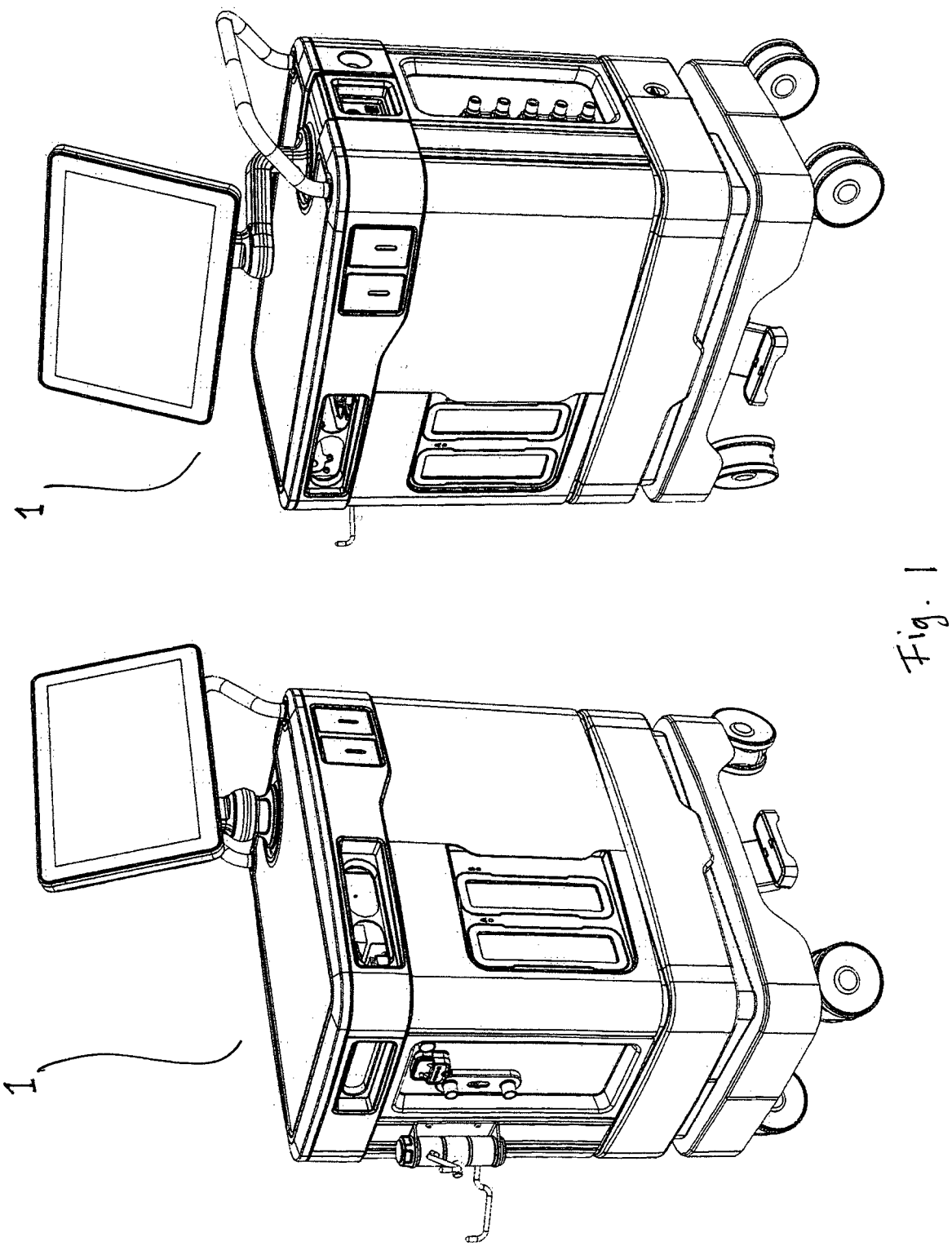
FIG. 1 is a perspective view of an apparatus for the respirating of patients according to the invention.

In FIG. 1 an apparatus 1 is shown for the respirating of patients, such as this can be used for ventilating at home, for anaesthesia or for intensive care, with provided therein, as is shown in FIG. 2, a line system 2 for the lead-through of respiratory gas. Connected to the line system 2 is a device 3 by means of which the pressure in the line system can be varied according to a certain respiratory pattern and two absorber devices 4 are present for the withdrawal from the line system of the carbon dioxide exhaled by the patient. These devices do not form part of the present invention. The line system further, as usual, is provided with a connection for the patient and with connections for the supply of the various components of the gas and with connections for the discharge of the various components of the gas (not shown in FIG. 1).

Figure 4B:
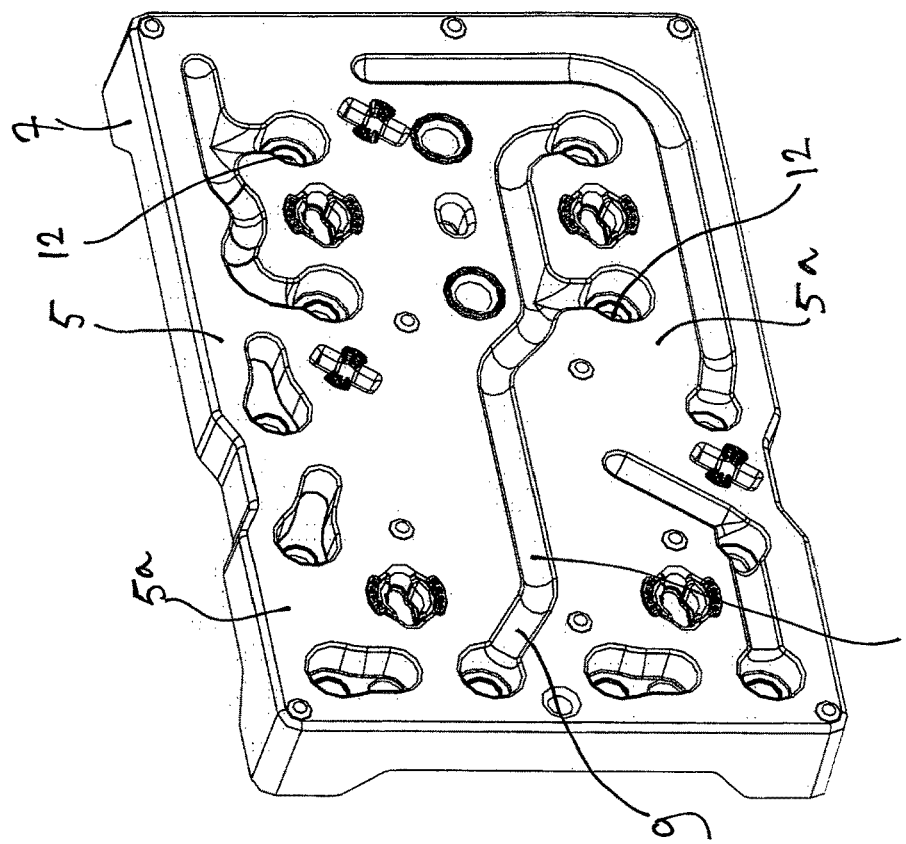
FIGS. 4a and 4b show a perspective view of an outer surface respectively inner surface of a first part 5 of the line system according to FIG. 3.

In FIG. 3, the line system 2, which is built up of a first part 5 and a second part 6 is shown. As can be seen in the FIGS. 4, 5 and 6, the parts 5, 6 are substantially plate-shaped. Each part has an inner surface 5a, 6a and an outer surface 5b, 6b. The parts 5, 6 are further provided with a side-edge 7, 8 flanged towards their outer surface 5b, 6b. By means of this, a more or less solid, rigid, construction is achieved.

As can be seen in FIG. 3, as well as in the FIGS. 8, 9a, 9b, 10 and 11, during use of the apparatus, the first part 5 and the second part 6 are intended to be placed with their inner surfaces 5a, 6a against each other and to be attached to each other. As can be seen in the FIGS. 4b, 5a, 6a, canals 9 are formed in the inner surfaces 5a, 6a, and canals 9 are open towards the inner surface 5a, 6a. The canals 9 are arranged in the inner surfaces 5a, 6a in the first part 5 and in the second part 6 in mirror image relative to each other, in such a way, that during placement of the inner surfaces 5a and 6a against each other, the open longitudinal side 10 of the canal 9 in the one inner surface 5a connects to the open longitudinal side 10 of the canal 9 in the other inner surface 6a. In this manner, when the parts are placed against each other, a flow-through pathway 11 is formed by the combined abutting canals 9, through which the respiratory- or anaesthetic gas can be led, as is shown in the FIGS. 2, 9a and 10.

In the example of an embodiment shown, the canals 9 are provided in both inner surfaces 5a, 6a. It is also possible to provide in just one of the two co-operating inner surfaces, for instance the inner surface 5a, a canal 9 or an otherwise deepened part, having a longitudinal side 10 that is open towards the inner surface 5a, so that, during placement on the more or less level inner surface 6a of the other part 6, the open longitudinal side 10 of the canal 9 or the deepened part is covered, and by means of which the desired flow-through pathway 11 is obtained too.

The parts can be manufactured from polyetherimide (PEI).

Figure 4A:
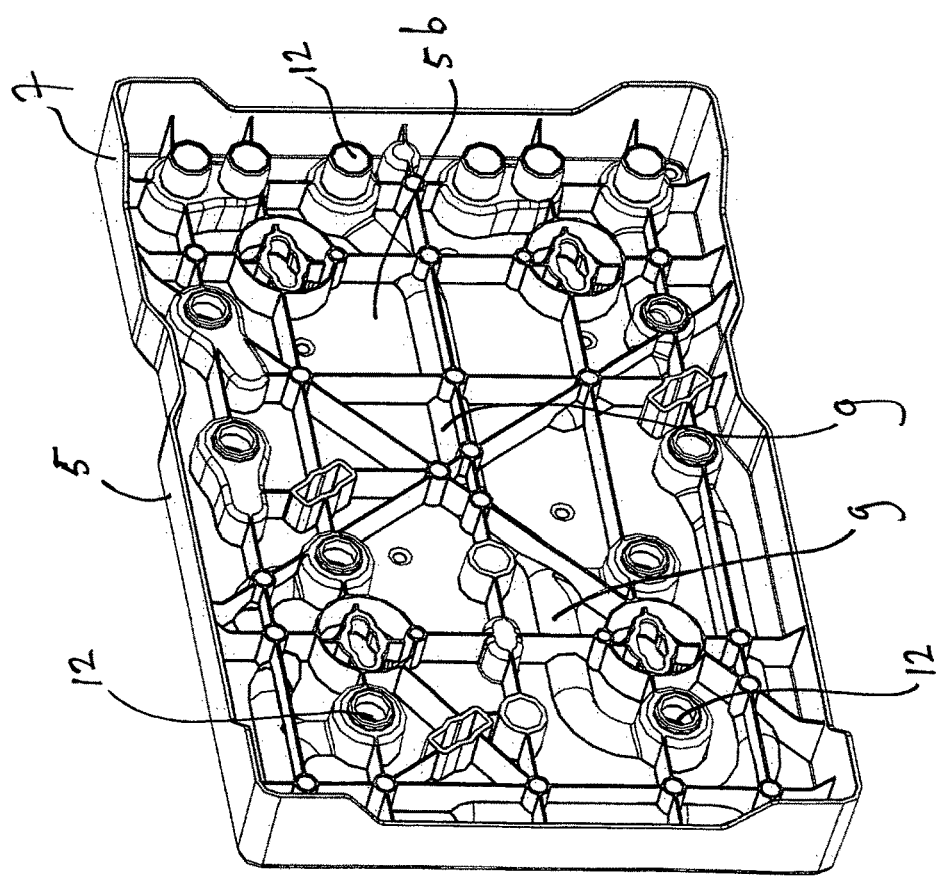
Figure 6B:
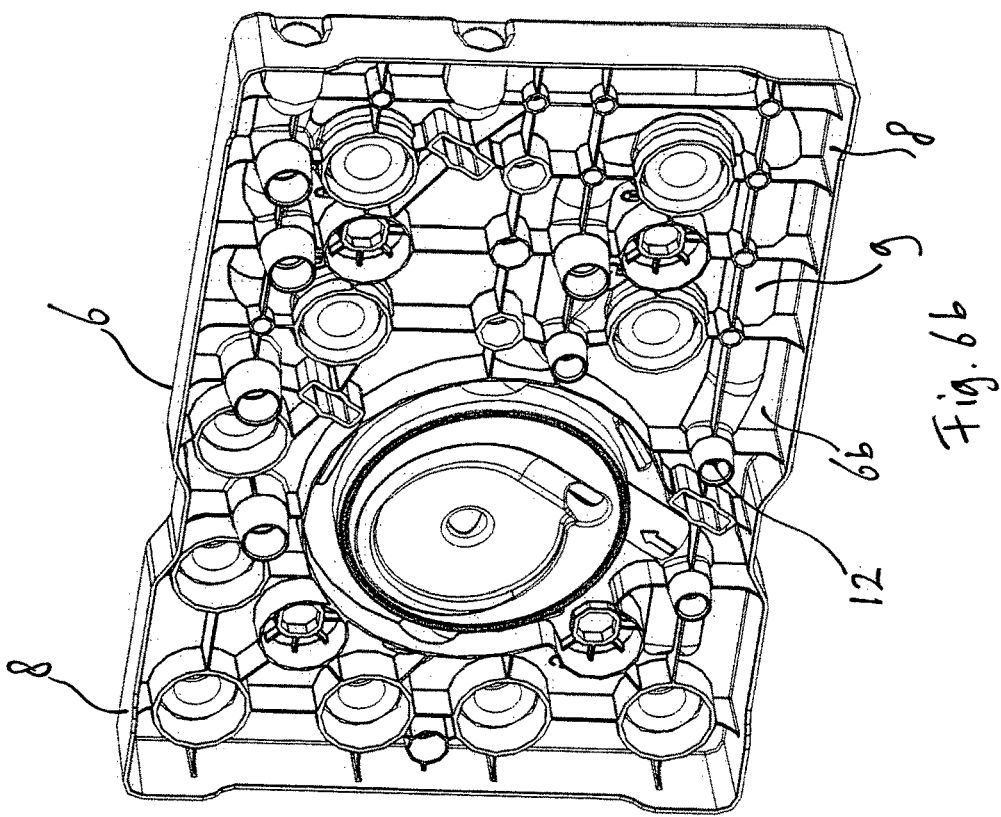
FIGS. 6a and 6b show a perspective view of an inner surface respectively an outer surface of the second part 6 of the line system, whereby the inner surface is coated with, in this example of an embodiment, a silicone layer.

As can further be seen in the FIGS. 4, 5 and 6, in the embodiment shown, the first part 5 and the second part 6 are provided with openings 12. At these openings 12, the further components of the respirating apparatus can be connected, such as the device 3 for the varying of the pressure in the line system, absorber devices 4 for the withdrawal from the line system of carbon dioxide, and the several connections for the supply and the discharge of components of the gas, to or with which openings 12 the canals 9 can be connected or in communication. At the location of these openings 12, further closing means can be provided.

The inner surface 5a, 6a of at least one of the parts 5, 6 is, in an efficient manner, provided with a layer of material, preferably a silicone layer. When the parts are attached to each other, this layer ensures a leak proof assembly of the parts attached to each other, which is of great importance because the respiratory gas may not escape unintentionally from the line system or the flow-through pathway.

Figure 6A:
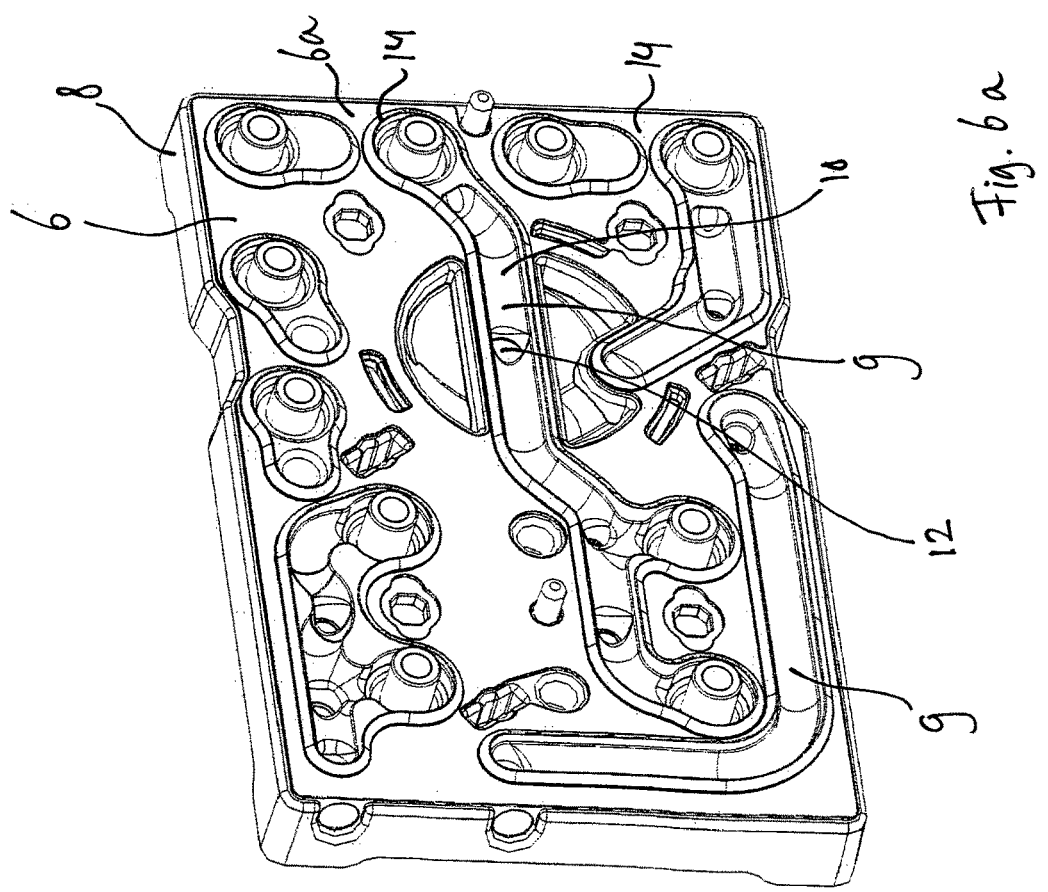
Figure 9A:
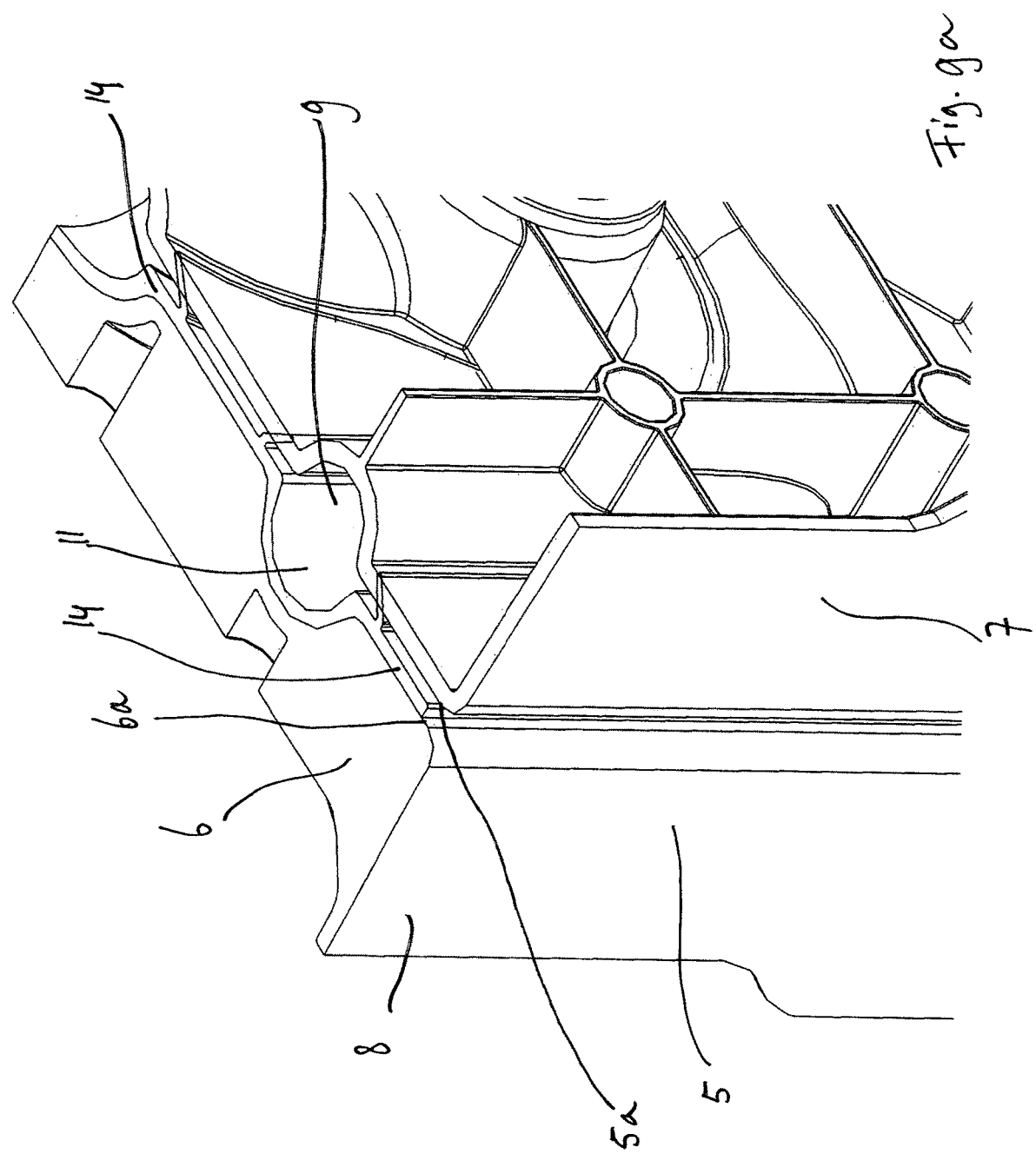
FIG. 9a shows a perspective view of a detail of the parts such as these are placed against each other.
Figure 9B:
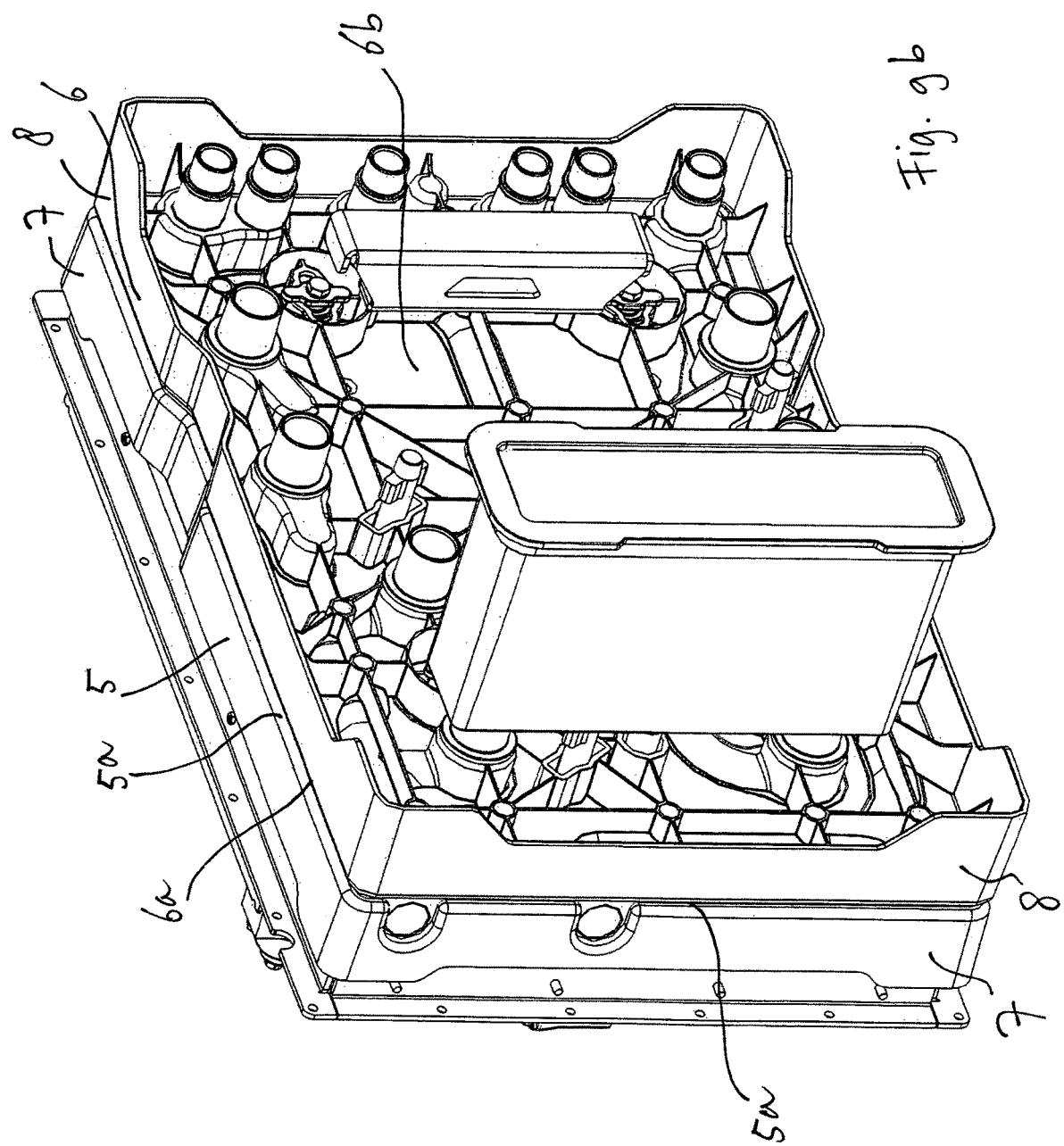
FIG. 9b shows a perspective view of the parts such as these are placed against each other.

In FIG. 6a, the second part 6, in the inner surface 6a of which the silicone layer 14 is shown. Thereby a few openings 15 of the openings 12 are covered by the layer, which can be seen in the detail of FIG. 7. The apparatus, at the location of an opening 12, can be provided with a closing means 13, as shown in FIG. 11, whereby the closing means 13 is displaceable into the flow-through pathway 11 for the opening and closing off of parts of the flow-through pathway 11. There, it is visible that the silicone layer 14, attached on the inner surface 6a of the second part 6, is situated between the closing means 13 and the first part 5, in such a way, that by means of the closing means 13, the silicone layer 14 can be pressed against the inner surface 5a of the first part 5.

Further on the outer surface 5b, 6b of the first part 5 and the second part 6, respectively, at the location of an opening 12, a cylindrical housing can be provided, from which a closing means is displaceable into the flow-through pathway, for the opening and closing off of parts of the flow-through pathway.

The line system assembly of the first part 5 and the second part 6 can be taken in and out relative to the respiratory apparatus 1. For the easy removal of the assembly out of the apparatus, this is provided with a handle (as can be seen at arrow A in FIG. 8). The first part 5 and the second part 6 are provided with means, by which these can be carefully attached to each other and detached again in a simple manner. After use of the apparatus, the assembly is removed from the apparatus and the first part 5 and the second part 6 are detached from each other. After this these are cleaned and dried. Because the canals are provided with an open part along their entire length, the inner surface of the canals is well reachable and the cleaning and drying of the line system or the flow-through pathway formed by the canals can be performed easily and thoroughly. After the cleaning and drying, the parts will be attached together again and placed into the apparatus, after which the further components can be connected to the line system by means of the openings that are present in the parts.

The invention claimed is:

1. An apparatus for respirating a patient, the apparatus comprising:
a line system for a lead-through of respiratory or anaesthesia gas, said line system having a first connection for the patient and a second connection to a supply of components of the respiratory or anaesthesia gas and a third connection for discharge of components of the respiratory or anaesthesia gas, wherein said line system is built from a first part and a second part, each of the first part and the second part being substantially plate-shaped, each of the first part and the second part having an inner surface and an outer surface, the first part and the second part being attached to each other with the inner surface of the first part and the inner surface of the second part facing each other, wherein a canal is formed in the inner surface of one of the first part and the second part, the canal having a longitudinal side that opens towards the inner surface of another of the first part and the second part such that an open side of the canal is covered by the inner surface of the another of the first part and the second part and a flow-through pathway is formed, the flow-through pathway adapted to allow the respiratory or anaesthesia gas to be led therethrough, wherein the inner surface of at least one of the first part and the second part has a layer of sealing or elastic material, wherein the layer of sealing or elastic material is attached to or coated onto the inner surface, wherein at least one of the first part and the second part has openings, the canal communicating with at least one of the openings, wherein the at least one of the openings is covered by the layer of sealing or elastic material, wherein a closure is positioned at the at least one of the openings, the closure being displaceable into the flow-through pathway so as to open or close the flow-through pathway, the closure causing the layer of sealing or elastic material to bear against the inner surface of the another of the first part and the second part.

2. The apparatus of claim 1, wherein the canal is formed in each of the inner surfaces of the first part and the second part, each of the canals having the longitudinal side open toward the inner surface, the longitudinal sides of the canals connecting with each other during displacement of the inner surfaces of the first part and the second part against each other, the canals forming the flow-through pathway.

3. The apparatus of claim 1, wherein the first part and the second part are detachable from to each other.

4. The apparatus of claim 1, wherein each of the first part and the second part is formed from a polyetherimide material.

5. The apparatus of claim 1, wherein the layer of material is formed of a silicone material.

\* \* \* \* \*